(12) United States Patent
Sauerberg et al.

(10) Patent No.: US 6,274,608 B1
(45) Date of Patent: Aug. 14, 2001

(54) COMPOUNDS, THEIR PREPARATION AND USE

(75) Inventors: Per Sauerberg, Farum; Anthony Murray, Hellerup; Lone Jeppesen, Virum; Paul Stanley Bury, København NV; Ingrid Pettersson, Frederiksberg, all of (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/551,700

(22) Filed: Apr. 18, 2000

Related U.S. Application Data
(60) Provisional application No. 60/134,972, filed on May 20, 1999.

(30) Foreign Application Priority Data

Apr. 20, 1999 (DK) ......................................... 00532

(51) Int. Cl.$^7$ ..................... A61K 31/426; C07D 277/34; C07C 59/13
(52) U.S. Cl. ..................... 514/369; 514/543; 514/569; 548/183; 560/56; 562/460
(58) Field of Search ............................. 548/183; 560/56; 562/460; 514/369; 569/543

(56) References Cited

FOREIGN PATENT DOCUMENTS

| | | |
|---|---|---|
| 0 337 689 | 10/1989 | (EP) . |
| 0 747 347 | 12/1996 | (EP) . |
| 0 903 343 | 3/1999 | (EP) . |
| WO 93/0606 | 4/1993 | (WO) . |
| WO 96/04261 | 2/1996 | (WO) . |
| WO 97/19052 | 5/1997 | (WO) . |
| WO 97/25042 | 7/1997 | (WO) . |
| WO 97/31907 | 9/1997 | (WO) . |
| WO 97/48672 | 12/1997 | (WO) . |
| WO 99/05801 | 2/1999 | (WO) . |
| WO 99/16758 | 4/1999 | (WO) . |

*Primary Examiner*—Robert Gerstl
(74) *Attorney, Agent, or Firm*—Reza Green, Esq.; Valeta A. Gregg, Esq.

(57) ABSTRACT

Disclosed are novel compounds of formula I

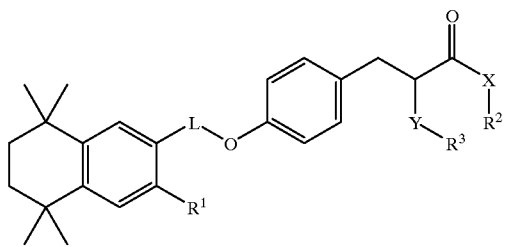

wherein $R^1$, $R^2$, $R^3$, L, X and Y are as defined in the specification. These compounds are useful in the treatment of conditions mediated by nuclear receptors, in particular the Retinoid X Receptor (RXR) and the Peroxisome Proliferator-Activated Receptor (PPAR) families. Such conditions include diabetes and obesity.

18 Claims, No Drawings

COMPOUNDS, THEIR PREPARATION AND USE

CROSS-REFERENCES TO RELATED APPLICATIONS

The present application claims priority under 35 U.S.C. 119 of U.S. provisional application 5 No. 60/134,972 filed May 20, 1999 and Danish application no. PA 1999 00532 filed Apr. 20, 1999, the contents of which are fully incorporated herein by reference.

BACKGROUND OF THE INVENTION

1. Field of the Invention

The present invention relates to novel compounds, pharmaceutical compositions containing them, methods for preparing the compounds and their use as medicaments. More specifically, compounds of the invention can be utilized in the treatment of conditions mediated by nuclear receptors, in particular the Retinoid X Receptor (RXR) and the Peroxisome Proliferator-Activated Receptor (PPAR) families. The compounds of the invention can also be used in combination with ligands for other nuclear receptors which are known to form dimeric complexes with RXR receptors, for example the Peroxisome Proliferator-Activated Receptor (PPAR) family.

2. Description of the Related Art

Non-insulin dependant diabetes mellitus (NIDDM, Type II diabetes) is a condition characterized by abnormal and ineffective insulin action and secretion. The entry of glucose from the blood into the cells of liver, skeletal muscle and adipose tissue is promoted by insulin action.

In the diabetic, tissues dependant on insulin are unable to assimilate glucose normally (insulin resistance), the result being an accumulation of glucose within the blood (hyperglycemia). Type II diabetes typically afflicts people over 40, and obesity is often a contributing factor. Regulation of diet and exercise can reduce to some extent the problems associated with NIDDM, but commonly insulin therapy or other oral hypoglycemic agents are the treatments of choice.

In addition to the range of insulin formulations, the most widely used hypoglycemic agents to date are sulphonylureas but in respective cases potentially fatal hyperinsulinemia or hypoglycemia can develop, and additional problems involving the cardiovascular, renal, neural and visual systems can also ensue.

More recently, a class of compounds termed thiazolidinediones (e.g., ciglitazone, pioglitazone, englitazone, troglitazone and BRL 49653) have been shown to reduce hyperglycemia by promoting insulin action without additional insulin secretion, and without causing undesirable hypoglycemia, even at elevated doses. Their effect is proposed to be a result of agonism at the PPAR receptor.

Even more recently, it has been reported that RXR agonists such as LGD 1069 and LG 100268 activate RXR/PPAR heterodimers, causing reduction in glucose, insulin and triglyceride levels in ob/ob and db/db mice (Mukherjee et al., Nature 1997, 386, 407410, Heyman and Mukherjee WO 97/10819). This effect is due to activation at the RXR part of the heterodimer. In turn these RXR/PPAR heterodimers can also be activated by PPAR agonists (e.g., thiazolidinediones) to give a similar effect, and it has been shown that at submaximal levels of either the RXR or PPAR agonist, addition of the complimentary agonist provides an additive and possibly synergistic response, and results in enhanced transcription and subsequently additional lowering of hyperglycemia, hyperinsulinemia and hypertriglyceridemia. It has therefore been proposed that compounds acting as agonists at both the RXR and PPAR receptors can be used as insulin sensitizers for the treatment of Type II diabetes and related symptoms.

Coronary artery disease (CAD) is the major cause of death in Type 2 diabetic and metabolic syndrome patients (i.e., patients that fall within the 'deadly quartet' category of impaired glucose tolerance, insulin resistance, hypertriglyceridemia and/or obesity).

The hypolipidemic fibrates and antidiabetic thiazolidinediones separately display moderately effective triglyceride-lowering activities although they are neither potent nor efficacious enough to be a single therapy of choice for the dyslipidemia often observed in Type 2 diabetic or metabolic syndrome patients. The thiazolidinediones also potently lower circulating glucose levels of Type 2 diabetic animal models and humans. However, the fibrate class of compounds are without beneficial effects on glycemia. Studies on the molecular actions of these compounds indicate that thiazolidinediones and fibrates exert their action by activating distinct transcription factors of the peroxisome proliferator activated receptor (PPAR) family, resulting in increased and decreased expression of specific enzymes and apolipoproteins respectively, both key players in regulation of plasma triglyceride content. Fibrates, on the one hand, are PPARα activators, acting primarily in the liver. Thiazolidinediones, on the other hand, are high affinity ligands for PPARγ acting primarily on adipose tissue.

Adipose tissue plays a central role in lipid homeostasis and the maintenance of energy balance in vertebrates. Adipocytes store energy in the form of triglycerides during periods of nutritional affluence and release it in the form of free fatty acids at times of nutritional deprivation. The development of white adipose tissue is the result of a continuous differentiation process throughout life. Much evidence points to the central role of PPARγ activation in initiating and regulating this cell differentiation. Several highly specialized proteins are induced during adipocyte differentiation, most of them being involved in lipid storage and metabolism. The exact link from activation of PPARγ to changes in glucose metabolism, most notably a decrease in insulin resistance in muscle, has not yet been clarified. A possible link is via free fatty acids such that activation of PPARγ induces Lipoprotein Lipase (LPL), Fatty Acid Transport Protein (FATP) and Acyl-CoA Synthetase (ACS) in adipose tissue but not in muscle tissue. This, in turn, reduces the concentration of free fatty acids in plasma dramatically, and due to substrate competition at the cellular level, skeletal muscle and other tissues with high metabolic rates eventually switch from fatty acid oxidation to glucose oxidation with decreased insulin resistance as a consequence.

PPARα is involved in stimulating β-oxidation of fatty acids. In rodents, a PPARα-mediated change in the expression of genes involved in fatty acid metabolism lies at the basis of the phenomenon of peroxisome proliferation, a pleiotropic cellular response, mainly limited to liver and kidney and which can lead to hepatocarcinogenesis in rodents. The phenomenon of peroxisome proliferation is not seen in man. In addition to its role in peroxisome proliferation in rodents, PPARα is also involved in the control of HDL cholesterol levels in rodents and humans. This effect is, at least partially, based on a PPARα-mediated transcriptional regulation of the major HDL apolipoproteins, apo A-I and apo A-II. The hypotriglyceridemic action of fibrates and fatty acids also involves PPARα and can be summarized as follows: (I) an increased lipolysis and clearance of remnant particles, due to changes in lipoprotein lipase and apo C-III levels, (II) a stimulation of cellular fatty acid uptake and their subsequent conversion to acyl-CoA derivatives by the induction of fatty acid binding protein and acyl-CoA synthase, (III) an induction of fatty acid-oxidation pathways, (IV) a reduction in fatty acid and triglyceride synthesis, and finally (V) a decrease in VLDL production. Hence, both enhanced catabolism of triglyceride-rich particles as well as reduced secretion of VLDL particles constitutes mechanisms that contribute to the hypolipidemic effect of fibrates.

A number of compounds have been reported to be useful in the treatment of hyperglycemia, hyperlipidemia and hypercholesterolemia (U.S. Pat. No. 5,306,726, PCT Publications nos. WO91/19702, WO 95/03038, WO 96104260, WO 94/13650, WO 94/01420, WO 97/36579, WO 97/25042, WO 95/17394, WO 99108501, WO 99/19313 and WO 99/16758).

DESCRIPTION OF THE INVENTION

The present invention relates to compounds of formula I

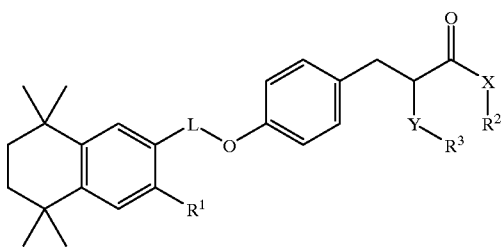

wherein $R^1$ is hydrogen or $C_{1-6}$-alkyl; and

X and Y are independently O, N or S; and $R^2$ is hydrogen or $C_{1-6}$-alkyl; and $R^3$ is hydrogen, $C_{1-8}$-alkyl, aryl or arylcarbonylaryl; and $R^2$ and $R^3$ may form a ring, which ring is optionally substituted with =O; and L is straight or branched $C_{1-6}$-alkyl optionally substituted with =O, OH or halogen; or a salt thereof with a pharmaceutically acceptable acid or base, or any optical isomer or mixture of optical isomers, including a racemic mixture, or any tautomeric forms.

In another preferred embodiment, the present invention is concerned with compounds of formula I wherein $R^1$ is hydrogen or $C_{1-6}$-alkyl; and X and Y are independently O, N or S; and $R^2$ is hydrogen or $C_{1-6}$-alkyl; and $R^3$ is hydrogen, $C_{1-8}$-alkyl, aryl or arylcarbonylaryl; and L is straight or branched $C_{1-6}$-alkyl optionally substituted with =O, OH or halogen.

In another preferred embodiment, the present invention is concerned with compounds of formula I wherein $R^1$ is hydrogen or $C_{1-6}$-alkyl; and X and Y are O, and $R^2$ is hydrogen or $C_{1-6}$-alkyl; and $R^3$ is hydrogen, $C_{1-8}$-alkyl, aryl or arylcarbonylaryl; and L is straight or branched $C_{1-6}$-alkyl optionally substituted with =O, OH or halogen.

In another preferred embodiment, the present invention is concerned with compounds of formula I wherein $R^1$ is hydrogen or $C_{1-4}$-alkyl; and X and Y are independently O, N or S; and $R^2$ and $R^3$ form a ring, which ring is optionally substituted with =O; and L is straight or branched $C_{1-4}$-alkyl optionally substituted with =O, OH or halogen.

In another preferred embodiment, the present invention is concerned with compounds of formula I wherein $R^1$ is hydrogen or $C_{1-4}$-alkyl; and X and Y are independently O, N or S; and $R^2$ is hydrogen or $C_{1-4}$alkyl; and $R^3$ is hydrogen or $C_{1-4}$-alkyl; and $R^2$ and $R^3$ may form a ring, which ring is optionally substituted with =O; and L is straight or branched $C_{1-4}$-alkyl optionally substituted with =O or OH.

In another preferred embodiment, the present invention is concerned with compounds of formula I wherein $R^1$ is hydrogen or $C_{1-4}$-alkyl; and X and Y are O; and $R^2$ is hydrogen or $C_{1-4}$-alkyl; and $R^3$ is hydrogen or $C_{1-4}$-alkyl; and L is straight or branched $C_{1-4}$-alkyl optionally substituted with =O or OH.

In another preferred embodiment, the present invention is concerned with compounds of formula I wherein $R^1$ is hydrogen or $C_{1-2}$-alkyl; and X and Y are O; and $R^2$ is hydrogen or $C_{1-2}$-alkyl; and $R^3$ is hydrogen or $C_{1-2}$-alkyl; and L is straight or branched $C_{1-4}$-alkyl.

In another preferred embodiment, the present invention is concerned with compounds of formula I wherein $R^1$ is hydrogen or $C_{1-2}$-alkyl; and X and Y are independently N or S; and $R^2$ and $R^3$ form a ring, which ring is substituted with =O; and is straight or branched $C_{1-4}$-alkyl.

Preferred compounds of the present invention are:

5-(4-(1-(3,5,5,8,8-Pentamethyl-5,6,7,8-tetrahydro-naphtalen-2-yl)-ethoxy)-benzyl)-thiazolidine-2,4-dione, 2-Ethoxy-3-(4-(1-(3,5,5,8,8-pentamethyl-5,6,7,8-tetrahydro-naphtalen-2-yl)-ethoxy)-phenyl)-propionic acid methyl ester, 2-Ethoxy-3-(4-(1-(3,5,5,8,8-pentamethyl-5,6,7,8-tetrahydro-naphtalen-2-yl)-ethoxy)-phenyl)-propionic acid, and (2S)-2-(2-Benzoylphenylamino)-3-(4-(1-(3,5,5,8,8-pentamethyl-5,6,7,8-tetrahydro-naphtalen-2-yl)-ethoxy)-phenyl)-propionic acid;

or a salt thereof with a pharmaceutically acceptable acid or base, or any optical isomer or mixture of optical isomers, including a racemic mixture, or any tautomeric forms.

In the above structural formulas and throughout the present specification, the following terms have the indicated meaning:

The term aryl represents, e.g., phenyl, pyridyl and the like.

The terms "$C_{1-n'}$-alkyl" wherein n' can be from 2 through 8, as used herein, represent a branched or straight alkyl group having from one to the specified number of carbon atoms. Typical $C_{1-8}$-alkyl groups include, but are not limited to, methyl, ethyl, n-propyl, iso-propyl, butyl, iso-butyl, sec-butyl, tert-butyl, pentyl, iso-pentyl, hexyl, iso-hexyl and the like.

The term "halogen" means fluorine, chlorine, bromine or iodine.

The term "arylcarbonylaryl" means two aryl groups connected to each other by a carbonyl group.

Certain of the above-defined terms may occur more than once in the above formula 1, and upon such occurrence each term shall be defined independently of the other.

The compounds of the present invention may have one or more asymmetric centers and it is intended that stereoisomers (optical isomers), as separated, pure or partially purified stereoiomers or racemic mixtures thereof are included in the scope of the invention.

The present invention also encompasses pharmaceutically acceptable salts of the present compounds. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

The pharmaceutically acceptable salts are prepared by reacting the compound of formula I with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol, etc. Mixture of solvents may be used. Organic bases like lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, fonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane, etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid, and the like wherever applicable or chiral bases such as brucine, cinchona alkaloids and their derivatives and the like. Commonly used methods are compiled by Jaques et al in "Enantiomers, Racemates and Resolution" (Wiley Interscience, 1981). More specifically the compound of formula I may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula I may be prepared by hydrolyzing the pure diastereomeric amide.

Various polymorphs of compound of formula I forming part of this invention may be prepared by crystallization of compound of formula I under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffraction or such other techniques.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

Furthermore, the present compounds of formula I can be utilized in the treatment and/or prevention of conditions mediated by nuclear receptors, in particular the Retinoid X Receptor (RXR) and the Peroxisome Proliferator-Activated Receptor (PPAR) families.

In a further aspect, the present invention relates to a method of treating and/or preventing Type I or Type II diabetes.

In a still further aspect, the present invention relates to the use of one or more compounds of formula I or pharmaceutically acceptable salts thereof for the preparation of a medicament for the treatment and/or prevention of Type I or Type II diabetes.

In a still further aspect, the present compounds are useful for the treatment and/or prevention of impaired glucose tolerance (IGT).

In a still further aspect, the present compounds are useful for the treatment and/or prevention of Type 2 diabetes.

In a still further aspect, the present compounds are useful for the delaying or prevention of the progression from IGT to Type 2 diabetes.

In a still further aspect, the present compounds are useful for the delaying or prevention of the progression from non-insulin requiring Type 2 diabetes to insulin requiring Type 2 diabetes.

In another aspect, the present compounds reduce blood glucose and triglyceride levels and are accordingly useful for the treatment and/or prevention of ailments and disorders such as diabetes and/or obesity.

In still another aspect, the present compounds are useful for the treatment and/or prophylaxis of insulin resistance (Type 2 diabetes), impaired glucose tolerance, dyslipidemia, disorders related to Syndrome X such as hypertension, obesity, insulin resistance, hyperglycemia, atherosclerosis, hyperlipidemia, coronary artery disease, myocardial ischemia and other cardiovascular disorders.

In still another aspect, the present compounds are effective in decreasing apoptosis in mammalian cells such as beta cells of Islets of Langerhans.

In still another aspect, the present compounds are useful for the treatment of certain renal diseases including glomerulonephritis, glomerulosclerosis, nephrotic syndrome, hypertensive nephrosclerosis.

In still another aspect, the present compounds may also be useful for improving cognitive functions in dementia, treating diabetic complications, psoriasis, polycystic ovarian syndrome (PCOS) and prevention and treatment of bone loss, e.g., osteoporosis.

The invention also relates to pharmaceutical compositions comprising, as an active ingredient, at least one compound of the formula I or any optical or geometric isomer or tautomeric form thereof including mixtures of these or a pharmaceutically acceptable salt thereof together with one or more pharmaceutically acceptable carriers or diluents.

Furthermore, the invention relates to the use of compounds of formula I or their tautomeric forms, their stereoisomers, their polymorphs, their pharmaceutically acceptable salts or pharmaceutically acceptable solvates thereof for the preparation of a pharmaceutical composition for the treatment and/or prevention of conditions mediated by nuclear receptors, in particular the Retinoid X Receptor (RXR) and the Peroxisome Proliferator-Activated Receptor (PPAR) families such as the conditions mentioned above.

The present invention also relates to a process for the preparation of the above said novel compounds, their derivatives, their analogs, their tautomeric forms, their stereoisomers, their polymorphs, their pharmaceutically acceptable salts or pharmaceutically acceptable solvates.

The compounds of this invention show a high degree of selectivity towards the RXR receptor family and the Peroxisome Proliferator-Activated Receptor (PPAR) families, and in particular have utility for the treatment of symptoms associated with noninsulin dependant diabetes mellitus.

In accordance with the present invention a compound of formula I can be prepared in the following ways:

By alkylating Ia under Friedel Craft condition with a suitable acid chloride containing linker L to give II

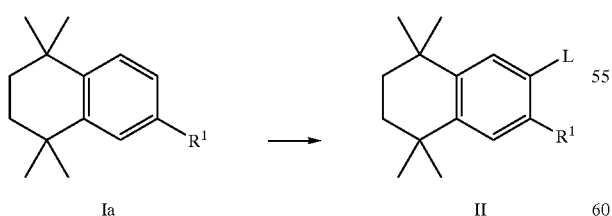

The intermediate II can then directly (e.g., via chloride) or after conversion of L, to contain an appropriate leaving group (e.g., reduction of carbonyl group to a hydroxy and then to phosphor under Mitsunobu conditions), be reacted with III to give IV

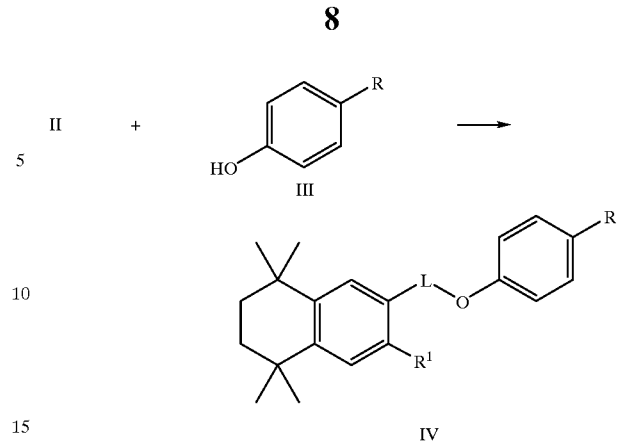

R can be either carboxaldehyde (CHO) or R is as defined in formula I and IV is then I.

b) When R is carboxaldehyde on either III or on IV, R can be reacted with the appropriate nucleopholic reagent (e.g., alkoxy-acetic acid ester-Wittig reagent to give the alkoxy-acrylic acid esters; or 2,4-thiazolidinedione to give benzylidene-thiazolidinediones) to give V The double bond can then be reduced to give I or the intermediate III (which can be coupled to II).

The intermediate III can also be a tyrosine derivative obtained by reacting tyrosine ester with the appropriate $R^3$-reagent (e.g., 2-benzoylcyclohexanone or alkylhalogenide).

Alcohols can be prepared by reduction of carboxylic acids and derivatives (for example, esters, acid chlorides) with metal hydrides. Aldehydes can be prepared by oxidation of alcohols (for example, with tetrapropyammonium perruthenate or dimethylsulphoxideloxalyl chloride) or reduction of carboxylic acid esters (for example, with diisobutyl aluminium hydride). Ketones can be prepared by reaction of carboxylic acid derivatives such as N-methyl-N-methoxy amides with Grignard reagents (Weinreb Tet. Lett. 1981, 22, 3815–3819). Ethers can be prepared from alcohols under standard Williamson conditions. Carboxylic acids can be prepared by oxidation of alcohols or aldehydes using mild oxidizing agents (for example, pyridinium dichromate in dimethylformamide).

In cases where a reaction may be inhibited by a reactive functional group contained in the molecule, for example alcohols, aldehydes, ketones or acids, the corresponding silyl ethers, acetals, ketals or esters can be prepared and later removed using standard protection/deprotection protocols known in the art. (Kocienski, *Protecting Groups*, Thieme 1994). In the case of $R^5$ being an amino group, protection as an amide by reaction with an activated acyl group is possible, alternatively it is possible to prepare the amino group at a later stage from the corresponding aryl halide by reactions known in the art.

Pharmacological Methods

In vitro PPAR alpha and PPAR Gamma Activation Activity

Principle

The PPAR gene transcription activation assays were based on transient transfection into human HEK293 cells of two plasmids encoding a chimeric test protein and a reporter protein respectively. The chimeric test protein was a fusion of the DNA binding domain (DBD) from the yeast GAL4 transcription factor to the ligand binding domain (LB D) of the human PPAR proteins. The PPAR LBD harbored in addition to the ligand binding pocket also the native activation domain (activating function 2=AF2) allowing the fusion protein to function as a PPAR ligand dependent transcription factor. The GAL4 DBD will force the fusion protein to bind only to Gal4 enhancers (of which none existed in HEK293 cells). The reporter plasmid contained a Gal4 enhancer driving the expression of the firefly luciferase protein. After transfection, HEK293 cells expressed the GAL4-DBD-PPAR-LBD fusion protein. The fusion protein will in turn bind to the Gal4 enhancer controlling the luciferase expression, and do nothing in the absence of ligand. Upon addition to the cells of a PPAR ligand, luciferase protein will be produced in amounts corresponding to the activation of the PPAR protein. The amount of luciferase protein is measured by light emission after addition of the appropriate substrate.

Methods

Cell culture and transfection: HEK293 cells were grown in DMEM+10% FCS, 1% PS. Cells were seeded in 96-well plates the day before transfection to give a confluency of 80 % at transfection. 0.8 $\mu$g DNA per well was transfected using FuGene transfection reagent according to the manufacturers instructions (Boehringer-Mannheim). Cells were allowed to express protein for 48 h followed by addition of compound.

Plasmids:

Human PPAR $\alpha$ and $\gamma$ was obtained by PCR amplification using cDNA templates from liver, intestine and adipose tissue respectively. Amplified cDNAs were cloned into pCR2.1 and sequenced. The LBD from each isoform PPAR was generated by PCR (PPAR$\alpha$: aa 167-C-term; PPAR$\gamma$: aa 165-C-term) and fused to GAL4-DBD by subcloning fragments in frame into the vector pM1 generating the plasmids pM1$\alpha$LBD and pM1$\gamma$LBD. Ensuing fusions were verified by sequencing. The reporter was constructed by inserting an oligonucleotide encoding five repeats of the Gal4 recognition sequence into the pGL2 vector (Promega).

Compounds:

All compounds were dissolved in DMSO and diluted 1:1000 upon addition to the cells. Cells were treated with compound (1:1000 in 200 $\mu$l growth medium including delipidated serum) for 24 h followed by luciferase assay.

Luciferase assay:

Medium including test compound was aspirated and 100 $\mu$l PBS incl. 1 mM Mg++ and Ca++ was added to each well. The luciferase assay was performed using the LucLite kit according to the manufacturers instructions (Packard Instruments). Light emission was quantified by counting SPC mode on a Packard Instruments top-counter.

Molecular Biology Characterization of RXR Activating Compounds

Competitive Binding Assay:

The method involves direct interaction between ligand and RXR and was analyzed by displacement of RXR bound [$^3$H] 9-cis RA (retinoic acid) in a competition assay essentially as described (Levin et al. *Nature* 1992, 355, 359–361 and Heyman et al. Cell 1992, 68, 397–406). Briefly, extracts of infected baculovirus cells expressing recombinant RXRa is used as source of binding activity. The compound of interest is incubated in the presence of [$^3$H] 9-cis RA with RXRa containing extract. Bound probe is separated from unbound through sephadex G50 chromatography. The amount of remaining bound [$^3$H] 9-cis RA was quantitated by scintillation counting.

RXR Transcriptional Activation:

The activation potential of a given compound was studied in a transient trans-activation assay, essentially as described (Heyman et al. Cell 1992, 68, 397406 and Tate et al. *Mol. Cel. Biol.* 1994, 14, 2323–2330). Expression plasmids encoding RXRa and a DR5 (direct repeat $N_5$) driven luciferase reporter plasmid was cotransfected into eucaryotic cells. Transfections also contained a plasmid constitutively expressing b-galactosidase (pCMVbgal) and carrier DNA (pGEM). 48 h after transfection cells were washed in PBS and re-fed medium containing ligand or vehicle (DMSO or Ethanol). Following overnight incubation cells were lysed and assayed for luciferse activity. Activation is expressed as the relative amount of luciferase activity (normalized to b-galactosidase activity) in treated versus untreated samples.

To determine the specificity of the ligands all were assayed on several nuclear receptors, most notably on RAR. For example, 9-cis retinoic acid (RA) activates both RXR and RAR whereas all-trans RA displays selectivity for RAR, (Heyman et al. Cell 1992, 68, 397406).

Pharmaceutical Compositions

In another aspect, the present invention includes within its scope pharmaceutical compositions comprising, as an active ingredient, an effective amount of at least one of the compounds of formula I or a pharmaceutically acceptable salt thereof, together with a pharmaceutically acceptable carrier or diluent.

The present compounds may also be administered in combination with one or more further pharmacologically active substances, e.g., selected from antiobesity agents, antidiabetics, antihypertensive agents, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipaselamylase inhibitors, RXR (retinoid X receptor) modulators or TR β agonists.

In one embodiment of the invention the antiobesity agent is leptin.

In another embodiment the antiobesity agent is dexamphetamine or amphetamine.

In another embodiment the antiobesity agent is fenfluramine or dexenfluramine.

In still another embodiment the antiobesity agent is sibutramine.

In a further embodiment the antiobesity agent is orlistat.

In another embodiment the antiobesity agent is mazindol or phentermine.

Suitable antidiabetics comprise insulin, GLP-1 (glucagon like peptide-1) derivatives such as those disclosed in WO 98/08871 to Novo Nordisk A/S, which is incorporated herein by reference as well as orally active hypoglycemic agents.

The orally active hypoglycemic agents preferably comprise sulphonylureas, biguanides, meglitinides, glucosidase inhibitors, glucagon antagonists such as those disclosed in WO 99/01423 to Novo Nordisk AIS and Agouron Pharmaceuticals, Inc., GLP-1 agonists, potassium channel openers such as those disclosed in WO 97126265 and WO 99/03861 to Novo Nordisk A/S which are incorporated herein by reference, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents as HMG CoA inhibitors (statins), compounds lowering food intake, and agents acting on the ATP-dependent potassium channel of the β-cells.

In one embodiment of the invention the present compounds are administered in combination with insulin.

In a further embodiment the present compounds are administered in combination with a sulphonylurea, e.g., tolbutamide, glibenclamide, glipizide or glicazide.

In another embodiment the present compounds are administered in combination with a biguanide, e.g., metformin.

In yet another embodiment the present compounds are administered in combination with a meglitinide, e.g., repaglinide.

In a further embodiment the present compounds are administered in combination with an α-glucosidase inhibitor, e.g., miglitol or acarbose.

In another embodiment the present compounds are administered in combination with an agent acting on the ATP-dependent potassium channel of the β-cells, e.g., tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent, e.g., cholestyramine, colestipol, clofibrate, gemfibrozil, lovastatin, pravastatin, simvastatin, probucol or dextrothyroxine.

In a further embodiment the present compounds are administered in combination with more than one of the above-mentioned compounds, e.g., in combination with a sulphonylurea and metformin, a sulphonylurea and acarbose, repaglinide and mefformin, insulin and a sulphonylurea, insulin and metformin, insulin, insulin and lovastatin, etc.

Furthermore, the present compounds may be administered in combination with one or more 5 antihypertensive agents. Examples of antihypertensive agents are p-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of the compounds according to the invention with one or more of the above-mentioned compounds and optionally one or more further pharmacologically active substances are considered to be within the scope of the present invention.

Pharmaceutical compositions containing a compound of the present invention may be prepared by conventional techniques, e.g. as described in Remington: The Science and Practise of Pharmacy, 19$^{th}$ Ed., 1995. The compositions may appear in conventional forms, for example capsules, tablets, aerosols, solutions, suspensions or topical applications.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, peanut oil, olive oil, gelatin, lactose, terra alba, sucrose, cyclodextrin, amylose, magnesium stearate, talc, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or coloring substances and the like, which do not deleteriously react with the active compounds.

The route of administration may be any route, which effectively transports the active compound to the appropriate or desired site of action, such as oral, nasal, pulmonary, transdermal or parenteral, e.g., rectal, depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet that may be prepared by conventional tabletting techniques may contain:
Core:

| | |
|---|---|
| Active compound (as free compound or salt thereof) | 5 mg |
| Colloidal silicon dioxide (AEROSIL) | 1.5 mg |
| Cellulose, microcryst. (AVICEL) | 70 mg |
| Modified cellulose gum (AC-DI-SOL) | 7.5 mg |
| Magnesium stearate | Ad. |

Coating:

| | |
|---|---|
| HPMC approx. | 9 mg |
| *Mywacett 9-40 T approx. | 0.9 mg |

*Acylated monoglyceride used as plasticizer for film coating.

The compounds of the invention may be administered to a mammal, especially a human in need of such treatment, prevention, elimination, alleviation or amelioration of diseases related to the regulation of blood sugar.

Such mammals include also animals, both domestic animals, e.g., household pets, and non-domestic animals such as wildlife.

The compounds of the invention are effective over a wide dosage range. For example, in the treatment of adult humans, dosages from about 0.05 to about 100 mg, preferably from about 0.1 to about 100 mg, per day may be used. A most preferable dosage is about 0.1 mg to about 70 mg per day. In choosing a regimen for patients, it may frequently be necessary to begin with a dosage of from about 2 to about 70 mg per day and when the condition is under control to reduce the dosage as low as from about 0.1 to about 10 mg per day. The exact dosage will depend upon the mode of administration, on the therapy desired, form in which administered, the subject to be treated and the body weight of the subject to be treated, and the preference and experience of the physician or veterinarian in charge.

Generally, the compounds of the present invention are dispensed in unit dosage form comprising from about 0.1 to about 100 mg of active ingredient together with a pharmaceutically acceptable carrier per unit dosage. Usually, dosage forms suitable for oral, nasal, pulmonary or transdermal administration comprise from about 0.001 mg to about 100 mg, preferably from about 0.01 mg to about 50 mg of the compounds of formula I admixed with a pharmaceutically acceptable carrier or diluent.

Any novel feature or combination of features described herein is considered essential to this invention.

EXAMPLES

The process for preparing compounds of formula I and preparations containing them is further illustrated in the following examples which, however, are not to be construed as limiting. The structures of the compounds are confirmed by either elemental analysis (MA) nuclear magnetic resonance (NMR) or mass spectrometry (MS). NMR shifts (d) are given in parts per million (ppm) and only selected peaks are given. mp is melting point and is given in ° C. Column chromatography was carried out using the technique described by W. C. Still et al, J. Org. Chem. 1978, 43, 2923–2925 on Merck silica gel 60 (Art 9385). Compounds used as starting materials are either known compounds or compounds which can readily be prepared by methods known per se.

Abbrevations:
TLC: thin layer chromatography
DMSO: dimethylsulfoxide
$CDCl_3$: deutorated chloroform
DMF: N,N-dimethylformamide
min: minutes
h: hours Example 1
1-(3,5,5,8,8-Pentamethyl-5,6,7,8-tetrahydro-naphthalen-2-yl)-ethanone To a suspension of $AlCl_3$ (2.88 g; 21.6 mmol) in methylene chloride (5 ml) was added over 15 minutes a solution of 1,1,4,4,6-pentamethyl-1,2,3,4-tetrahydro-naphthalene (4.0 g; 20 mmol) and acetyl chloride (1.6 ml; 21.6 mmol) in methylene chloride (20 ml) at 0° C. The reaction mixture was stirred for 30 minutes and ice cooled water (50 ml) was added. The organic phase was separated and the water phase was further extracted with methylene chloride (3×30 ml). The combined organic phases were first washed with brine then dried before evaporated. The residue was purified by column chromatography using hexane:methylene chloride (1:1) to give the title compound in 4.9 g (100%) yield.

1-(3,5,5,8,8-Pentamethyl-5,6,7,8-tetrahydro-naphthalen-2-yl)-ethanol

To a solution of 1-(3,5,5,8,8-pentamethyl-5,6,7,8-tetrahydro-naphthalen-2-yl)-ethanone (500 mg; 2.0 mmol) in dry THF (5 ml) was added slowly LiAlH$_4$ (80 mg; 2.0 mmol) at 0° C. The reaction mixture was stirred for 3 hours, and then water (20 ml) was added. Ether (50 ml) was added and the mixture was filtered through filter aid. The organic phase was separated and the water phase was extracted with ether. The combined organic phases were dried and evaporated to give the title compound in 504 mg (100%) yield.

4-(1-(3,5,5,8,8-Pentamethyl-5,6,7,8-tetrahydro-naphtalene-2-yl)-ethoxy)-benzaldehyde A solution of 1-(3,5,5,8,8-pentamethyl-5,6,7,8-tetrahydro-naphthalen-2-yl)-ethanol (246 mg; 1.0 mmol), triphenylphosphine (262 mg; 1.0 mmol), diethyl azodicarboxylate (0.153 ml; 1.0 mmol) and 4-hydroxybenzaldehyde (183 mg; 1.5 mmol) in THF (20 ml) was stirred at 0° C. for 1.5 hours and for 16 hours at room temperature. Water was added (20 ml) and the mixture was extracted with methylene chloride (3×25 ml). The combined organic phases were dried and evaporated. The residue was purified on column chromatography using ethyl acetate: hexane (1:3) as eluent. Yield 180 mg.

5-(4-(1-(3,5,5,8,8-pentamethyl-5,6,7,8-tetrahydro-naphtalen-2-yl)-ethoxy)-benzylidene)-thiazolidine-2,4-dione A mixture of 4-(1-(3,5,5,8,8-pentamethyl-5,6,7,8-tetrahydro-naphtalene-2-yl)-ethoxy)-benzaldehyde (350 mg; 1.0 mmol), 2,4-thiazolidinedione (129 mg; 1.1 mmol), piperidine (1 drop) and acetic acid (1 drop) in toluene (10 ml) was refluxed for 3 hours using a water separator. Upon cooling to room temperature the product precipitated. Filtration gave the title compound in 325 mg (72%) yield.

Example 2

5-(4-(1-(3,5,5,8,8-Pentamethyl-5,6,7,8-tetrahydro-naphtalen-2yl)-ethoxy)-benzyl)-thiazolidine-2,4-dione 5-(4-(1-(3,5,5,8,8-pentamethyl-5,6,7,8-tetrahydro-naphtalen-2-yl)-ethoxy)-benzylidene)-thiazolidine-2,4-dione (200 mg; 0.44 mmol) was first attempted hydrogenated with Pd/C 5% (235 mg) in dioxane (50 ml) at 100° C. for 10 hours. Filtration and extraction of the mixture showed a mixture of starting material and product (185 mg). The mixture was then dissolved in MeOH (25 ml) and magnesium (100 mg) was added. The reaction mixture was stirred over the week end at room temperature and then evaporated. The residue was dissolved in water and ethyl acetate and the pH was adjusted to 7 with 1 N HCl. The mixture was stirred for 5 minutes after which the organic phase was separated. The organic phase was dried and evaporated, and the residue was purified on column chromatography using methylene chloride: methanol (15:1) as eluent to give the title compound in 76 mg (38%) yield. Compound 1.

Example 3

2-Ethoxy-3-(4-(1-(3,5,5,8,8-pentamethyl-5,6,7,8-tetrahydro-naphtalen-2-yl)-ethoxy)-phhenyl)-propionic acid methyl ester Magnesium (160 mg; 6.7 mmol) was added to a suspension of 2-ethoxy-3-(4-(1-(3,5,5,8,8-pentamethyl-5,6,7,8-tetrahydro-naphtalen-2-yl)-ethoxy)-phenyl)-acrylic acid ethyl ester (160 mg; 0.37 mmol) in methanol (25 ml) at room temperature. The reaction mixture was stirred for 16 hours at room temperature. The reaction mixture was evaporated to half volume. Water (100 ml) was added and the pH was adjusted to 7 with 1 N HCl after which the mixture was extracted with ethyl acetate (2×75 ml). The combined organic phases were dried and evaporated. The crude product was purified on column chromatography using methylene chloride as eluent to give the title compound in 108 mg (67%) yield. Compound 2.

Example 4

2-Ethoxy-3-(4-(1-(3,5,5,8,8-pentamethyl-5,6,7,8-tetrahydro-naphtalen-2-yl)-ethoxy)-phenyl)-propionic acid A solution of 2-ethoxy-3-(4-(1-(3,5,5,8,8-pentamethyl-5,6,7,8-tetrahydro-naphtalen-2-yl)-ethoxy)-phenyl)-propionic acid methyl ester (108 mg; 0.24 mmol) in methanol (15 ml) was treated with 1 N NaOH and the reaction mixture was stirred for 16 hours. The reaction mixture was evaporated and 0.1 N HCl (20 ml) and ethyl acetate (50 ml) was added. The organic phase was separated and the water phase was further extracted with ethyl acetate (50 ml). The combined organic phases were dried and evaporated to give crude product. Purification on column chromatography using methylene chloride:methanol (15:1) as eluent gave the title compound in 105 mg (100%) yield. Compound 3.

Example 5

(2S)-2-(2-Benzoylphenylamino)-3-(4-(1 -(3,5,5,8,8-pentamethyl-5,6,7,8-tetrahydro-naphtalen-2-yl)-ethoxy)-phenyl)-propionic acid methyl ester A solution of 1-(3,5,5,8,8-pentamethyl-5,6,7,8-tetrahydronaphthalen-2-yl)-ethanol (184 mg; 0.75 mmol), triphenylphosphine (268 mg; 1.0 mmol), diethyl azodicarboxylate (0.161 ml; 1.0 mmol) and (2S)-2-((2-benzoylphenyl)amino)-3-(4-hydroxyphenyl)-propionic acid methyl ester (190 mg; 0.5 mmol) in THF (10 ml) was stirred at 0° C. for 1.5 hours and for 16 hours at room temperature. The reaction mixture was evaporated and the residue was purified on column chromatography using methylene chloride as eluent. Yield 118 mg.

(2S)-2-(2-Benzoylphenylamino)-3-(4-(1-(3.5,5.8,8-pentamethyl-5,6,7,8-tetrahydro-naphtalen-2-yl)-ethoxy)-phenyl)-propionic acid To a solution of (2S)-2-(2-Benzoylphenylamino)-3-(4(1-(3,5,5,8,8-pentamethyl-5,6,7,8-tetrahydro-naphtalen-2-yl)-ethoxy)-phenyl)-propionic acid methyl ester (100 mg; 0.17 mmol) in THF (12 ml) was added a solution of lithium hydroxide (16 mg; 0.37 mmol) in water (8 ml). The reaction mixture was stirred at room temperature for 4 hours and 1 N HCl was added to pH 6. The mixture was extracted with methylene chloride (2×50 ml). The combined organic phases were dried and evaporated. The product was crystallized as the L-lysine salt from methanol-hexanes. Yield 95 mg. Compound 4.

What is claimed is:

1. A compound of formula I

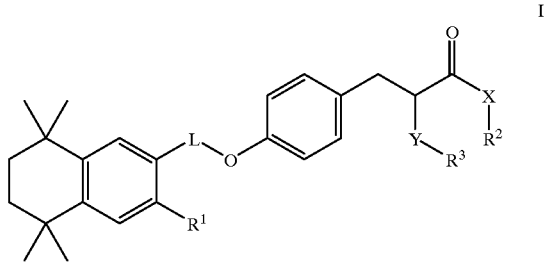

wherein $R^1$ is hydrogen or $C_{1-6}$-alkyl; and

X and Y are independently O, N or S; and $R^2$ is hydrogen or $C_{1-6}$-alkyl; and $R^3$ is hydrogen, $C_{1-8}$-alkyl, aryl or arylcarbonylaryl; and
$R^2$ and $R^3$ may form a ring, which ring is optionally substituted with =O; and
L is straight or branched $C_{1-6}$-alkyl optionally substituted with =O, OH or halogen;
or a salt thereof with a pharmaceutically acceptable acid or base, or any optical isomer or mixture of optical isomers, or any tautomeric forms.

2. A compound of claim 1, wherein $R^1$ is hydrogen or $C_{1-6}$-alkyl; and
X and Y are independently O, N or S; and
$R^2$ is hydrogen or $C_{1-6}$-alkyl; and
$R^3$ is hydrogen, $C_{1-8}$-alkyl, aryl or arylcarbonylaryl; and
L is straight or branched $C_{1-6}$-alkyl optionally substituted with =O, OH or halogen.

3. A compound of claim 1, wherein R' is hydrogen or $C_{1-6}$-alkyl; and
X and Y are O, and
$R^2$ is hydrogen or $C_{1-4}$-alkyl; and
$R^3$ is hydrogen, $C_{1-8}$-alkyl, aryl or arylcarbonylaryl; and
L is straight or branched $C_{1-6}$-alkyl optionally substituted with =O, OH or halogen.

4. A compound of claim 1, wherein $R^1$ is hydrogen or $C_{1-6}$-alkyl; and
X and Y are independently O, N or S; and
$R^2$ and $R^3$ form a ring, which ring is optionally substituted with =O; and
L is straight or branched $C_{1-4}$-alkyl optionally substituted with =O, OH or halogen.

5. A compound of claim 1, wherein $R^1$ is hydrogen or $C_{1-4}$-alkyl; and
X and Y are independently O, N or S; and
$R^2$ is hydrogen or $C_{1-4}$-alkyl; and
$R^3$ is hydrogen or $C_{1-4}$-alkyl; and
$R^2$ and $R^3$ may form a ring, which ring is optionally substituted with =O; and
L is straight or branched $C_{1-4}$-alkyl optionally substituted with =O or OH.

6. A compound of claim 1, wherein $R^1$ is hydrogen or $C_{1-4}$-alkyl; and
X and Y are O; and
$R^2$ is hydrogen or $C_{1-4}$-alkyl; and
$R^3$ is hydrogen or $C_{1-4}$-alkyl; and
L is straight or branched $C_{1-4}$-alkyl optionally substituted with =O or OH.

7. A compound of claim 1, wherein $R^1$ is hydrogen or $C_{1-2}$-alkyl; and
X and Y are O; and
$R^2$ is hydrogen or $C_{1-2}$-alkyl; and
$R^3$ is hydrogen or $C_{1-2}$-alkyl; and
L is straight or branched $C_{1-4}$-alkyl.

8. A compound of claim 1, wherein $R^1$ is hydrogen or $C_{1-2}$-alkyl; and
X and Y are independently N or S; and
$R^2$ and $R^3$ form a ring, which ring is substituted with =O; and
L is straight or branched $C_{1-4}$-alkyl.

9. A compound of claim 1 selected from the group consisting of
5-(4-(3,5,5,8,8-Pentamethyl-5,6,7,8-tetrahydro-naphtalen-2-yl)-ethoxy)-benzyl)-thiazolidine-2,4-dione,
2-Ethoxy-3-(4-(1-(3,5,5,8,8-pentamethyl-5,6,7,8-tetrahydro-naphtalen-2-yl)-ethoxy)-phenyl)-propionic acid methyl ester,
2-Ethoxy-3-(4-(1 -(3,5,5,8,8-pentamethyl-5,6,7,8-tetrahydro-naphtalen-2-yl)-ethoxy)-phenyl)-propionic acid, and
(2S)-2-(2-Benzoylphenylamino)-3-(4-(1-(3,5,5,8,8-pentamethyl-5,6,7,8-tetrahydro-naphtalen-2-yl)-ethoxy)-phenyl)-propionic acid;
or a salt thereof with a pharmaceutically acceptable acid or base, or any optical isomer or mixture of optical isomers, or any tautomeric forms.

10. A pharmaceutical composition comprising, as an active ingredient, an effective amount of a compound of claim 1, together with a pharmaceutically acceptable carrier or diluent.

11. The pharmaceutical composition of claim 10 in unit dosage form, comprising from about 0.05 to about 100 mg of the compound.

12. The pharmaceutical composition of claim 11 in unit dosage form, comprising from about 0.1 to about 50 mg of the compound.

13. The pharmaceutical composition of claim 10 which is administered by the oral, nasal, transdermal, pulmonary, or parenteral route.

14. A method of treating or preventing conditions mediated by nuclear receptors, comprising administering to a subject in need thereof an effective amount of a compound of claim 1.

15. The method of claim 14, wherein the nuclear receptors are the Retinoid X Receptor (RXR) and the Peroxisome Proliferator-Activated Receptors (PPAR).

16. A method of treating or preventing diabetes and/or obesity, the method comprising administering to a subject in need thereof an effective amount of a compound of claim 1.

17. The method of claim 14, wherein the effective amount of the compound is in the range of from about 0.05 to about 100 mg per day.

18. The method of claim 17, wherein the effective amount of the compound is in the range of from about 0.1 to about 50 mg per day.

* * * * *